(12) United States Patent
Gulsen et al.

(10) Patent No.: US 9,078,587 B2
(45) Date of Patent: Jul. 14, 2015

(54) METHOD AND APPARATUS FOR PHOTOMAGNETIC IMAGING

(71) Applicant: The Regents of the University of California, Oakland, CA (US)

(72) Inventors: Gultekin Gulsen, Irvine, CA (US); David Thayer, Irvine, CA (US); Yuting Lin, Mission Viejo, CA (US); Mehmet Burcin Unlu, Instanbul (TR)

(73) Assignee: The Regents of the University of California, Oakland, CA (US)

( * ) Notice: Subject to any disclaimer, the term of this patent is extended or adjusted under 35 U.S.C. 154(b) by 121 days.

(21) Appl. No.: 13/654,346

(22) Filed: Oct. 17, 2012

(65) Prior Publication Data

US 2013/0102880 A1 Apr. 25, 2013

Related U.S. Application Data (60) Provisional application No. 61/550,258, filed on Oct. 21, 2011.

(51) Int. Cl.
| A61B 5/055 | (2006.01) |
| A61B 5/01 | (2006.01) |
| A61B 5/00 | (2006.01) |
| G01R 33/48 | (2006.01) |

(52) U.S. Cl.
CPC .............. *A61B 5/055* (2013.01); *A61B 5/0093* (2013.01); *A61B 5/01* (2013.01); *G01R 33/4804* (2013.01)

(58) Field of Classification Search
CPC ........ A61B 5/0093; A61B 5/01; A61B 5/055; G01R 33/4804
See application file for complete search history.

(56) References Cited

U.S. PATENT DOCUMENTS

| 4,900,303 | A * | 2/1990 | Lemelson ..................... 604/514 |
| 6,542,769 | B2 * | 4/2003 | Schwamm et al. ........... 600/420 |
| 6,618,608 | B1 * | 9/2003 | Watkins et al. ............... 600/412 |
| 7,351,252 | B2 * | 4/2008 | Altshuler et al. ............... 607/88 |
| 8,246,611 | B2 * | 8/2012 | Paithankar et al. ............... 606/9 |
| 8,554,305 | B2 * | 10/2013 | Tailor et al. ................... 600/420 |
| 8,647,335 | B2 * | 2/2014 | Markus ........................... 606/15 |
| 2004/0268421 | A1 * | 12/2004 | Tearney et al. .................... 800/3 |
| 2005/0240107 | A1 * | 10/2005 | Alfano et al. ................. 600/476 |
| 2008/0097194 | A1 * | 4/2008 | Milner ........................... 600/425 |
| 2009/0143669 | A1 * | 6/2009 | Harms et al. .................. 600/410 |
| 2010/0016689 | A1 * | 1/2010 | Kanayama et al. ........... 600/316 |
| 2010/0022860 | A1 * | 1/2010 | Rebec et al. .................. 600/316 |
| 2010/0042004 | A1 * | 2/2010 | Dhawan ......................... 600/476 |
| 2010/0069898 | A1 * | 3/2010 | O'Neil et al. ..................... 606/9 |

* cited by examiner

*Primary Examiner* — Ruth S Smith
(74) *Attorney, Agent, or Firm* — Knobbe Martens Olson and Bear LLP (57) ABSTRACT

A method for photomagnetic imaging of tissue includes the steps of heating the tissue using light; measuring a change in temperature of the tissue with magnetic resonance thermometry; and creating an optical property map from the measured change in temperature. An apparatus for performing photomagnetic imaging of tissue which includes a light source to heat the tissue, a magnetic resonance imaging system to measure a change in temperature of the tissue, and a data processor to generate an optical property map from the measured change in temperature. An optical property map of tissue photomagnetic imaging of tissue produced by: heating the tissue using light; measuring a change in temperature of the tissue with magnetic resonance thermometry; and creating an optical property map from the measured change in temperature.

16 Claims, 8 Drawing Sheets
(4 of 8 Drawing Sheet(s) Filed in Color)

United States Patent US 9,078,587 B2

METHOD AND APPARATUS FOR PHOTOMAGNETIC IMAGING

The present application is related to U.S. Provisional Patent Application Ser. No. 61/550,258, filed on Oct. 21, 2012, which is incorporated herein by reference and to which priority is claimed pursuant to 35 USC 119.

BACKGROUND

1. Field of the Technology

The disclosure relates to the field of imaging, particularly photomagnetic imaging using laser heating and magnetic resonance imaging.

2. Description of the Prior Art

Over the last few decades, a variety of in vivo imaging techniques have been developed using a broad spectrum of technologies to obtain structural, functional, and molecular information about the tissue under investigation. One category of these techniques is optical imaging. Optical imaging works by shining laser light on tissue and then measuring the results. Optical imaging can provide functional information, such as hemoglobin concentration, and can visualize exogenous contrast agents as well as molecular and functional markers. In vivo optical imaging extends across a wide range of applications, from the organ to the cellular levels.

One type of optical imaging, diffuse optical tomography (DOT) works by measuring with optical fibers how the path of light is altered by absorption and scattering as it passes through tissue. DOT can penetrate up to 10 centimeters of tissue, but only offers low-resolution images (>5 mm) due to the highly scattering nature of tissue. DOT can provide absorption maps at multiple wavelengths and hence, functional information such as tissue endogenous chromophore or exogenous contrast agent distribution. Furthermore. DOT can serve as a powerful molecular imaging tool in its fluorescent mode by providing the concentration and lifetime maps of a fluorescent molecular probes.

Significant effort has been expended on developing multimodality imaging techniques to improve the resolution of optical imaging beyond DOT. One intriguing method combines optical and ultrasound techniques, and is called photoacoustic imaging. Photo-acoustic tomography (PAT) is a type of photo-acoustic imaging which utilizes a short-pulsed laser (~10 ns) to very rapidly raise the temperature of tissue. PAT works by creating an ultrasound wave as a result of the thermoelastic expansion of the tissue caused by the rise in temperature. This ultrasound wave is then detected by ultrasound transducers. Because the ultrasound waves scatter much less than optical waves in biological tissue, the overall resolution of the resulting image is improved dramatically. PAT can provide the same functional information as DOT, but with much higher resolution (~1 mm). However, this is achieved at the cost of tissue depth penetration, as PAT is only capable of penetrating about 3 centimeters of tissue.

A recently developed type of photoacoustic imaging, photo-acoustic microscopy (PAM), modifies PAT by using high frequency ultrasonic transducers. PAM captures even higher resolution images (~10 µm) than can be obtained with PAT, but the improved resolution comes at a much greater limitation on the imaging depth, as PAM can only penetrate to a depth of about 3 millimeters of tissue.

All the techniques mentioned above have a common weakness, in that they are only capable of acquiring data from the boundary of the medium. In the above mentioned techniques, two dimensional projection data is collected from many views to construct three dimensional images. The ultimate aims of these tomographic imaging techniques are to estimate the unknown distribution of optical properties in the whole volume imaged by using a finite number of measurements taken from the boundaries of the volume. This is achieved by solving an inverse problem, a framework used to convert observations and measurements into good estimations of physical properties—in this case, the physical properties of a volume of tissue. This problem is difficult to solving using both DOT and photoacoustic imaging techniques, because the number of unknown factors dwarfs the number of measurements that can be taken. Generally, however, photoacoustic imaging has been found to be superior to DOT, because of its utilization of ultrasound waves instead of optical photons The first step of analyzing photoacoustic imaging data is to reconstruct the acoustic pressure source map. During this process, the medium is generally assumed to be acoustically homogeneous, and tissue heterogeneity may reduce the quantitative accuracy in this step. The second step is to convert the pressure map into an absorbed energy map. The third and the final step is to reconstruct the absorption and scattering maps. The greatest difficulty faced by this process is overcoming the fact that the absorbed energy at any particular point is a function of not only the absorption properties of the tissue, but also the local light fluence. The light fluence itself depends on both the light absorption and the light scattering properties of the tissue. Recently, there have been several different attempts to solve this challenging step.

Another major problem with photoacoustic imaging comes from the light distribution within tissue. The optical fluence decreases drastically as the photons travels from the illumination point at the boundary into areas deeper into the tissue. Because of this, noise-generating optoacoustic (OA) sources are predominantly created by the optical energy absorbed within the first centimeter of thicker tissues. These OA sources dramatically expand the dynamic range of the OA signals, thereby reducing the resolution and contrast of the image. Reflections of the ultrasonic waves generated by strong OA sources from the acoustic boundaries, such as echogenic areas inside the tissue, physical tissue boundaries, and the housing of piezoelectric transducers, can all be a source of acoustic noise. This noise not only creates artifacts in resulting images, but also reduces the ability of photoacoustic imaging systems to detect small lesions.

Another limitation of photoacoustic imaging is revealed by acoustic impedance mismatches between different tissue types, such as between bones or skull and the surrounding soft tissues.

A further limitation of photoacoustic imaging is that it requires a physical conducting medium in contact with and between the ultrasound transducers and the tissue under examination. Usually, this requires immersion of the tissue in a liquid, such as water. This creates practical difficulties, such as requiring test animals such as mice to be immersed in a tank in a hanging position, resulting in shifting of internal organs and changes to the physiological characteristics of the animal.

One of the primary applications of photoacoustic imaging is breast imaging for detection of tumor masses. Several systems for photoacoustic imaging of the breast have been reported in prior art. One such system, the laser optoacoustic imaging system (LOIS), has been estimated to be sufficient for single-pulse imaging of 6 to 11 mm tumors throughout the whole imaging slice of the breast. However, visualization of smaller masses still remains elusive.

BRIEF SUMMARY

To solve these and other problems, a new technique has been invented, called photomagnetic imaging (PMI). PMI works by using a continuous wave (CW) laser to heat tissue with laser light, and then measuring the resulting temperature changes with an MRI machine operating in a magnetic resonance thermometry (MRT) mode. The measured temperature change at any point is determined to be proportional to the tissue absorption coefficient at that point Using PMI, the absorption and scattering coefficients of tissue can be determined by using a finite element-based inverse problem to obtain absorption and scattering maps. These maps are obtained by taking measurements at different wavelengths. The resulting absorption coefficient data can then be used to estimate the concentrations of oxyhemoglobin, deoxyhemoglobin, fat, and water in the tissue. These concentrations are extremely useful in determining whether cancers are benign or malignant.

PMI's principal advantage over other methods of optical imaging is that it can detect the same tissue properties as in DOT or photoacoustic imaging, but operates at the resolution of an MRI machine. This results in significantly better localization and resolution of the resulting images than in DOT, without the requirement for tissue contact as in PAT or PAM. Furthermore, PMI does not have the same acoustic problems resulting from the scattering of waves through acoustically heterogeneous tissues as seen in photoacoustic imaging techniques, allowing PMI to image deeper than PAT. Finally, because PMI measures the entire volume of the tissue using magnetic imaging thermometry, the technology is not limited to external measurements. This eliminates the need to assume tissues are homogeneous and eliminates image artifacts due to unwanted reflections of sound waves. Furthermore, because measurement of PMI uses an MRI machine, it does not require tissue contact or external fiber bundles, and measurements can instead be taken when using catheter-based illumination fibers. These illumination fibers can be used to deliver continuous wave (CW) laser light into tissues not readily accessible externally, allowing for potential imaging applications in many internal parts of the body.

The proposed PMI system can be implemented as a low-cost add on to the currently available MR systems due to utilization of cheaper continuous wave lasers as well as absence of an optical detection system. The implementation of the PMI on current MRI coils is simple and convenient. Cumbersome and complex interfaces present significant barriers for many other kinds of multi-modality approaches. MRI is currently the standard modality for clinical management for breast cancer. Hence, PMI will impact breast cancer management whenever MRI is used from diagnosis to therapy monitoring. For instance, a light pain-free compression (5 cm-6 cm) PMI breast imaging system can be designed with illumination from both sides. The combination of MRI & PMI may not only impact clinical success, but also speed up development of optical molecular probes by providing accurate distribution of molecular optical probes in breast. Furthermore, PMI can be translated for lymph node imaging for which the high resolution capability is important to see the nodes deep in the tissue. Finally, catheter based PMI might find interesting applications besides breast cancer in the future. For example, a tiny illumination fiber may be used to deliver the light into the tissue for one-shot PMI illumination. Potential catheter based PMI applications may include: prostate imaging via a urethral probe, interrogating prostate tissue to help MR guided HIFU therapy for prostate cancer, and pancreas imaging due to its thin structure.

More specifically, the illustrated embodiments of the invention include a method for photomagnetic imaging of tissue including the steps of heating the tissue using light; measuring a change in temperature of the tissue with magnetic resonance thermometry; and creating an optical property map from the measured change in temperature.

The method further includes the step of injecting one or more optical contrast agents into the tissue.

The step of heating the tissue using light includes heating the tissue with laser light incident upon the tissue, which light is a continuous wave laser incident upon the tissue.

The step of heating the tissue using light includes heating the tissue using laser light incident upon tissue by delivery through a flexible illuminating optical fiber, which in some embodiments may be adapted to be inserted into a body cavity.

The step of measuring the resulting change in temperature of the tissue with magnetic resonance thermometry includes measuring the change in temperature one or more times utilizing multiple wavelengths of laser light.

The method further includes recovering absorption and scattering coefficients using a finite element-based inverse problem.

The step of creating an optical property map from the measured change in temperature includes creating an absorption map or scattering map from the measured change in temperature.

The step of creating an optical property map from the measured change in temperature includes creating an optical property map based on a measure of the distribution of the injected optical contrast agent.

The method further includes the step of determining an estimated concentration of tissue oxyhemoglobin, deoxyhemoglobin, fat, and/or water.

The method further includes the step of using the estimated concentration to diagnose a disease, evaluate a therapeutic treatment response, or to visualize or evaluate a result of an experimental application.

The step of using the estimated concentration to diagnose a disease includes using the estimated concentration to diagnose a cancer which is determined as benign or malignant based on the determined data.

The method further includes determining a metabolic property of tissue from the determined estimated concentration.

The method further includes the step of evaluating the performance of one or more of the optical contrast agents.

The illustrated embodiments of the invention also include within their scope an apparatus for performing photomagnetic imaging of tissue which includes a light source to heat the tissue, a magnetic resonance imaging system to measure a change in temperature of the tissue, and a data processor to generate an optical property map from the measured change in temperature.

The data processor further determines an estimated concentration of tissue oxyhemoglobin, deoxyhemoglobin, fat, and/or water to diagnose a disease, evaluate a therapeutic treatment response, or to visualize or evaluate a result of an experimental application.

The data processer uses the estimated concentration to diagnose a cancer which is determined as benign or malignant based on the determined data.

The illustrated embodiments of the invention also include within their scope an optical property map of tissue photomagnetic imaging of tissue produced by: heating the tissue using light; measuring a change in temperature of the tissue with magnetic resonance thermometry; and creating an optical property map from the measured change in temperature.

The optical property map may be produced by further determining an estimated concentration of tissue oxyhemoglobin, deoxyhemoglobin, fat, and/or water to diagnose a disease, evaluate a therapeutic treatment response, or to visualize or evaluate a result of an experimental application.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The specification contains at least one drawing executed in color. Copies of this patent or patent application publication with color drawing(s) will be provided by the Office upon request and payment of the necessary fee.

FIG. 5($a$) is a diagram of a multi-point PMI setup with sources S1-S8.

FIG. 5($b$) is a diagrammatic map of a photon density profile for multipoint PMI. The dotted line S5 shows the profile of photon density for a single source. The dashed line S1 shows the profile of photon density for a single source placed opposite the blue source. The dark solid line S1+S5 shows the addition of those two sources. The light solid line labeled. All is the addition of all eight sources, S1-S8. The long-short dashed line labeled Noise Level shows the noise level.

FIG. 5($c$) is a graph comparing the normalized singular values of DOT, single point PMI, and multipoint PMI as a function of the singular value number. This graph clearly shows the advantage of multi-point PMI in its higher signal-to-noise ratio and greater number of singular values above the noise level.

FIGS. 6$a$-6$d$ is a collection of data maps of a phantom containing nine inclusions of 2 mm in diameter. The images have similar levels of absorption coefficient but different temperature increases due to the spatially varying photon density.

FIG. 7$a$-7$e$ is a collection of in vivo data maps of a rat. These four temperature maps were obtained while the laser is on and under ANSI limit. The last images shows the superimposition of anatomic image and temperature map obtained at 88 s. The yellow arrow shows the probing depth, which is 1.5 cm. The red arrows indicate the illumination area.

FIGS. 8$a$-8$c$ illustrate the results of a breast sized phantom. FIG. 8$a$ is a temperature difference map for the third frame (16-24 sec). The red arrows indicates the illumination points. The bottom probe delivers 30% more light than the top one and still under ANSI limit. FIG. 8$b$ is a reconstructed absorption map using four temperature frames acquired in 32 seconds (8-second each). The two 5 mm objects positioned 2 cm below both surface are successfully recovered with 5% and 15% error based on the peak value, respectively. FIG. 8$c$ is a graph of the profile of the phantom of FIGS. 8$a$ and 8$b$ showing that full width half maximum (FWHM) of the recovered objects are very close to their real size ~5 mm.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Magnetic resonance thermometry refers to a collection of techniques using magnetic resonance imaging (MRI) to non-invasively measure temperature. MR thermometry has found its most widespread use in monitoring thermal ablation therapies where temperature monitoring is necessary for measuring thermal dose. Several MR imaging parameters can be used to find either relative or absolute temperatures. These parameters are: proton resonant frequency (PRF); the diffusion coefficient; T1 and T2 relaxation times; magnetization transfer; proton density; and temperature-sensitive contrast agents. When choosing an MR thermometry approach, there are several factors to consider. Some of these include sensitivity, linearity, the ability to make absolute or relative measurements, acquisition time, tissue-type specificity, and sensitivity to artifacting.

Proton density is linearly dependent on temperature with sensitivity about 0.30±0.01% between 37° C. and 80° C. The low sensitivity requires high signal-to-noise ratio (SNR) and acquisition times are slow. T1 relaxation time is also temperature-dependent, increasing with increasing temperature. Sensitivity is around 1% but varies in different tissues. Using T1 times to determine temperature is also very time-consuming. T2 relaxation time also increases nonlinearly with temperature. It is difficult to use T2 times to measure temperature changes so it is seldom used. The diffusion coefficient is also temperature-dependent. It is very sensitive, but is also very sensitive to motion artifacts, is nonlinear, and varies by tissue type. Magnetization transfer can potentially be used for temperature measurements, but is insensitive and strongly tissue type dependent. The PRF of water is also temperature dependent. Either spectroscopic imaging or phase imaging can be used to utilize the temperature-dependence of the PRF. Spectroscopic imaging tend to be low-resolution and slow, but can be used to find absolute temperatures. Phase mapping is the most accepted and widely used approach because it can be fast, has high spatial resolution, and is tissue-type independent. The phase mapping approach is preferable mainly because of its sensitivity and speed.

Figure 3:
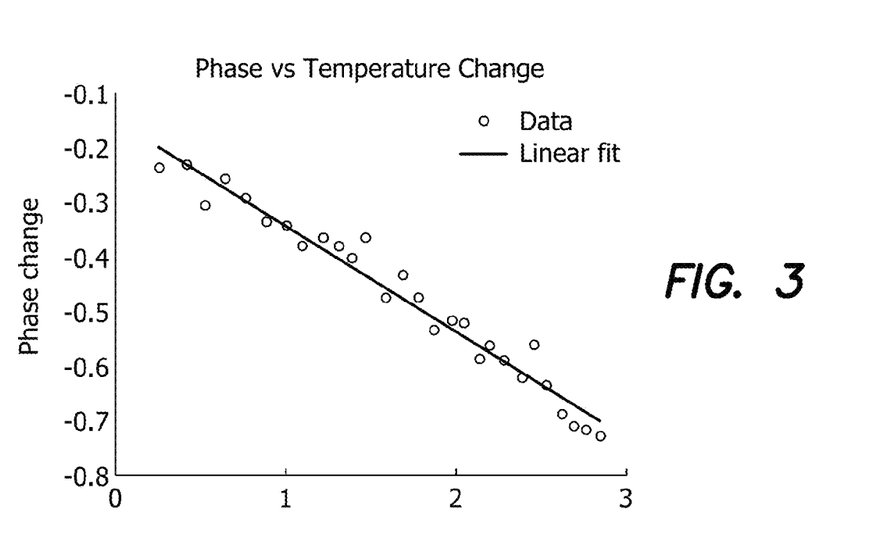
FIG. 3 is a graph of phase change against temperature change, which illustrates the phase changes obtained from the MR measurement versus the temperature by the fiber optic probe. The scope of this curve provides the calibration coefficient required to convert phase images to temperature maps. The linear trend shows that the drift in the MRI phase measurements is negligible.

To measure possible drift in the MRI phase measurements, a MRI phantom may be used as a test object. First, the change in the temperature of the phantom without any light exposure may be monitored. The phantom may be kept refrigerated and then placed in the MR/Optical interface. MR measurements may be acquired over a period of 30 minutes. Due to the ambient temperature of the MR scanner room, the phantom may be observed to warm up over this period. A MR compatible fiber optic temperature probe may be used to calibrate MR temperature measurements. Its accuracy may be nearly +/−0.1 C.°. FIG. 3 is a graph which shows the phase changes obtained from the MR measurements (around the region of the fiber optic probe tip) versus the temperature measurements by the probe itself. As seen from FIG. 3, the MR measurements may be linear with the fiber temperature sensor readings indicating that the drift was negligible over 30 minutes. Moreover, the phase measurements may be linearly related to temperature. The temperature of the agar phantom changed nearly 3 degrees due to the ambient temperature of the MR scanner room. The slope of this curve provided the calibration coefficient required to convert phase images into temperature maps. The linear trend over 30 minutes shows that the drift in the MRI phase measurements is negligible.

Figure 4:
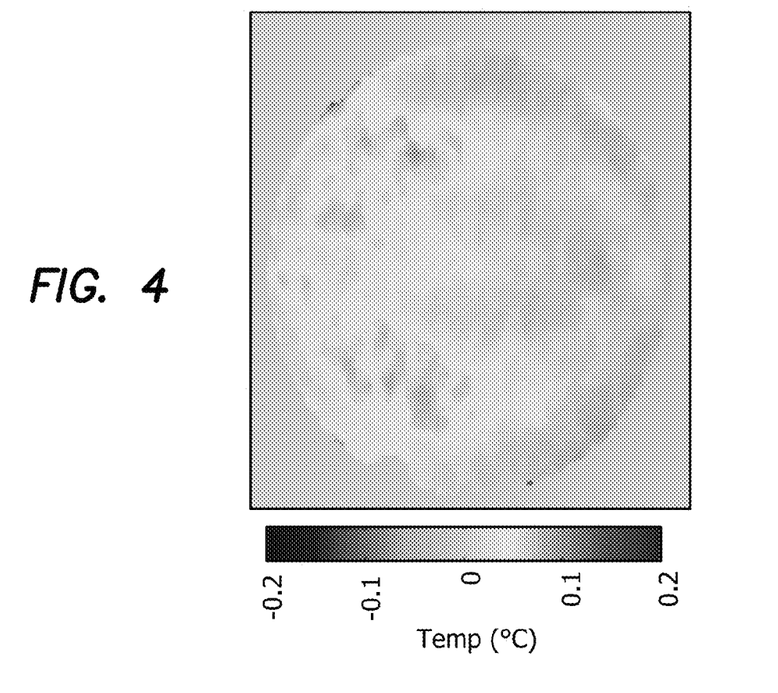
FIG. 4 is a data map of the temperature difference between two successive images from a 25 mm diameter agar phantom. The standard deviation is about 0.05° C.

The standard MR sequence utilizes a single slice gradient echo sequence with 256 readout steps with oversampling, 128 phase encoding steps with no oversampling, a TR=60 ms, a TE=32 ms, a field of view (FOV) of 60 mm, a slice thickness of 5 mm, a 30° flip angle, and an overall acquisition time of 10 s. FIG. 4 shows the difference between two successive temperature data map images from a 25 mm diameter agar phantom without any heating. The standard deviation between successive temperature measurements was around 0.05° C.

A diffusion equation may be used to model the light transport in tissue-like phantom. The frequency domain representation of the optical diffusion equation may be written as:

$$\vec{\nabla} \cdot D(\vec{r})\vec{\nabla}\phi(\vec{r}, \omega) - \left[\mu_a(\vec{r}) + \frac{i\omega n}{c_0}\right]\phi(\vec{r}, \omega) = -S(\vec{r}, \omega) \quad (1)$$

where $\phi(r, \omega)$ is the optical light fluence rate (W.mm$^{-2}$), $S(r, \omega)$ is the optical light source (W.mm$^{-3}$), w is the optical light source modulation frequency, D(r) is the photon diffusion coefficient, $\mu_a$ is the photon absorption coefficient, $c_0$ is the speed of the light in vacuum, and n is the index of refraction of the medium.

The next step in photomagnetic imaging is to solve a coupled equation. First, the diffusion equation (Eq. 1) above may be used to find the distribution of light in the medium. Then the bio-heat equation should be used to model heat transfer in the tissue:

$$\rho \cdot c \cdot \frac{\partial T(\vec{r}, t)}{\partial t} = \nabla k \nabla T(\vec{r}, t) + Q_R + Q_M + w_b \cdot c_b(T_a(\vec{r}, t) - T(\vec{r}, t)) \quad (2)$$

where, $\rho$, c, and k denotes density, specific heat, and thermal conductivity of the tissue; $c_b$ is the specific heat of blood and $w_h$ is blood perfusion rate. $Q_R$ and $Q_M$ represent the imposed spatial heating and metabolic heat generation, respectively. The last term is the sink term due to blood flow, where $T_a$ is the supplying arterial blood temperature and T is the tissue temperature. The temperature distribution varies with the time so the solution is time dependent. The following boundary condition may be used:

$$-k\nabla T = h(T-T_0) \quad (3)$$

where h is the heat transfer coefficient between the surface of the medium and the surrounding medium at temperature $T_0$. During the forward solution, first photon density distribution in the medium ($\phi$) may be calculated using Eq. 1. After that, the energy deposition of due to the photons propagating in the tissue may be calculated as:

$$Q_R = \phi \cdot \mu_a \quad (4)$$

and used as input to the bio-heat equation (Eq. 2) as the imposed spatial heating due to the light. The image reconstruction for the photomagnetic imaging seeks a minimum between the measured and calculated data, and may be written as:

$$\chi(\mu)^2 = \sum_i^M (T_{m,i}(t) - T_{c,i}(\mu, t))^2 + \sum_j^{NE} \lambda_j (I(\mu_j - \mu_0))^2 \quad (5)$$

Where $T_{m,i}$ is the measured data, $T_{c,i}$ is the calculated data using the forward solver, M is the total number of measurements, NE is the number of elements, and $\mu_j$ is the absorption coefficients. Here, the measurements are high resolution temperature maps provided by the MRI. Therefore, the matrix equation becomes:

$$\Delta\mu = (J^T J + \lambda I)^{-1} J^T (T_m - T_c) \quad (6)$$

where the Jacobian matrix is:

$$J_{ij} = \frac{\partial T_{c,i}}{\partial \mu_j} \quad (7)$$

and $\Delta\mu$ is the update vector that is the difference between the true value and the estimated value of absorption coefficient, I is the identity matrix, and $\lambda$ is the Tikhonov regularization parameter.

Figure 5A:
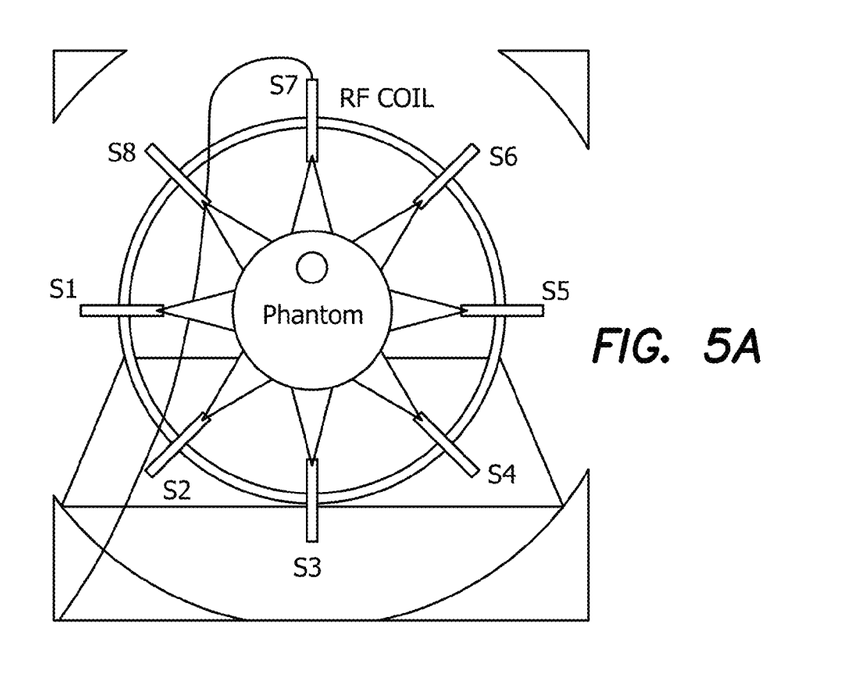

Simulations may be performed to analyze the effect of simultaneous multiple point illumination on the depth penetration and stability of the inverse problem rather than sequential illumination from each point. A 40 mm diameter synthetic phantom may be used for simulations. FIG. 5a is a diagram of the experimental setup for this synthetic data acquisition scheme or a multi-point PMI setup. The set-up is positioned on the patient couch in the MRI bore. Radially distributed eight optical probes (S1 ... S8) simultaneously illuminate the sample at the center of the MRI RE coil inside the MRI magnet positioned above the patient couch (portions of which magnet and couch are shown in FIG. 5a), although, sequential illumination is a viable alternative, Holes (not shown) on the MRI RF-coil provide a mounting point for each of the fiber probes and allow their operation. The phantom is shown diagrammatically as a sphere with an off-center spherical inclusion. Each laser is shown with a diverging beam impinging on the phantom. Simulations show that multipoint illumination performance is superior compared to sequential illumination.

Figure 5B:
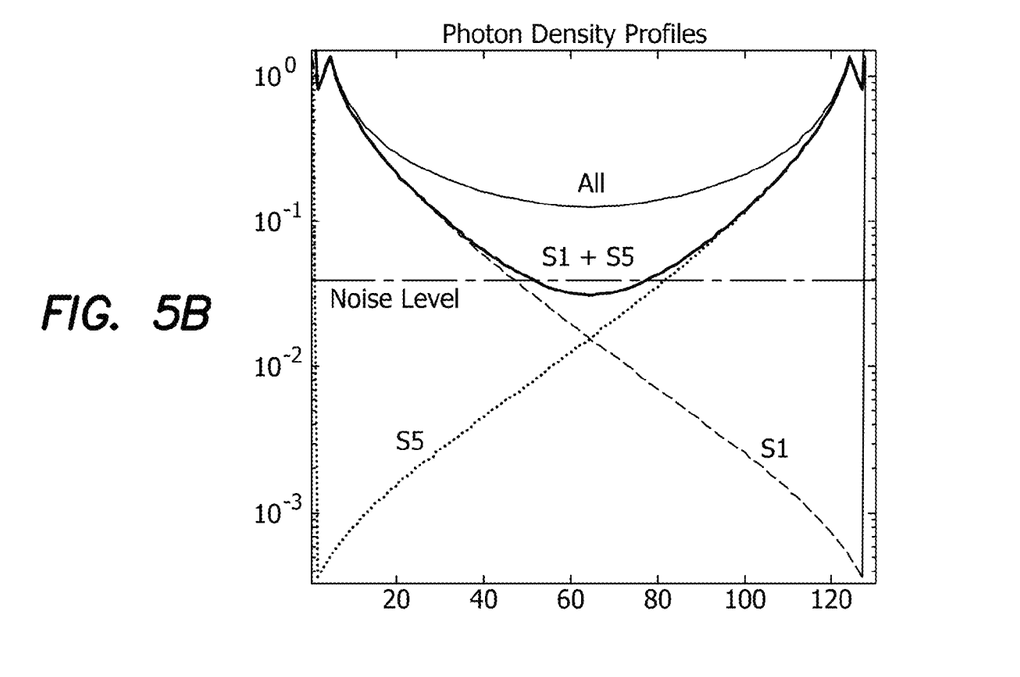
Figure 5C:
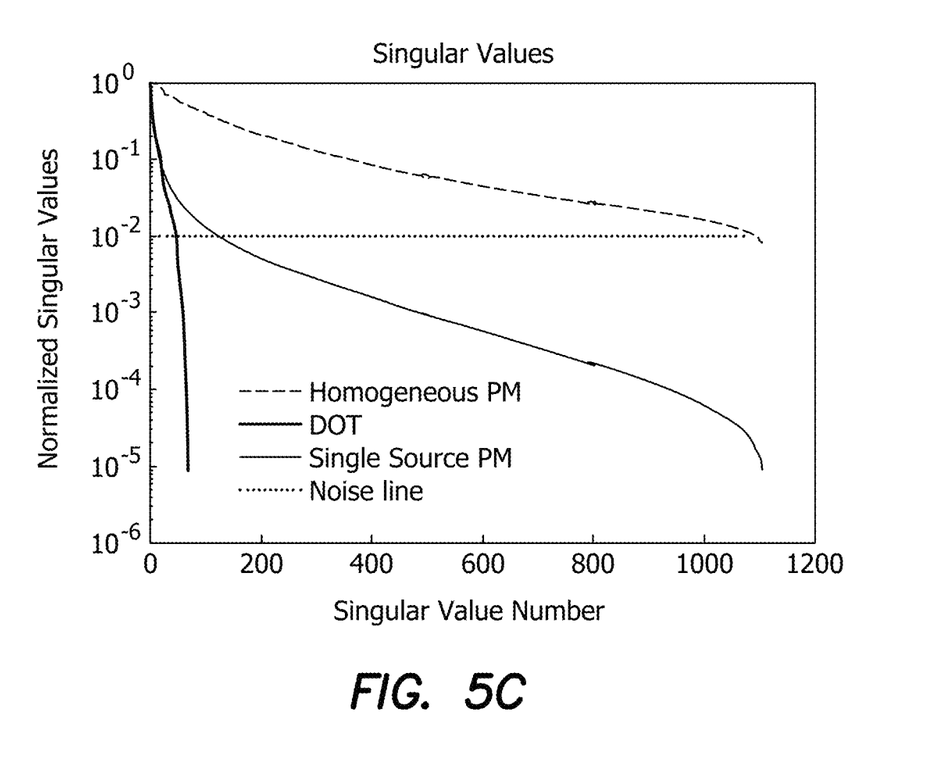

FIG. 5b compares the photon density profile for a single source, two sources placed at the opposite sites, and multipoint illumination using all eight sources in FIG. 5a. It is clear that the signal-to-noise ratio (SNR) increases with the number of sources. The posedness of DOT and PMI may be compared using singular value decomposition (SVD), a tool for analyzing the invertibility of inverse problems. In the case of a nonlinear problem, such as DOT or PMI, the Jacobian update matrix gives the relationship between changes in the object space and the resulting change in the imaging space. Singular values below 1% of the highest singular value may be considered noise and any information contained by the basis vectors weighted by these singular values may be considered "lost" in the forward problem. The distribution of singular values may give a view of the invertibility of a problem. As seen from FIG. 5c, a higher number of singular values are above the noise level when an increasing number of sources may be used. While improving data quality and stability of the inverse problem, multipoint data acquisition will not reduce the sensitivity of the Jacobian operator due to acquisition of data from the whole volume, compared to standard diffuse optical imaging.

To show the utility of photomagnetic imaging, multiple examples of embodiments of the present invention are provided:

Example 1

Phantom Studies

Figure 6A:
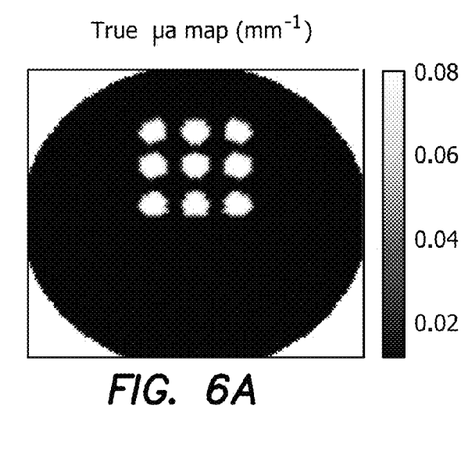
Figure 6B:
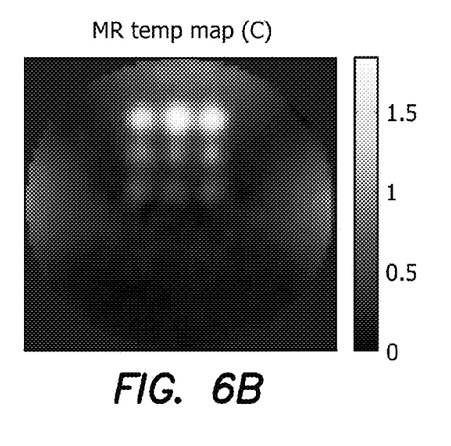
Figure 6C:
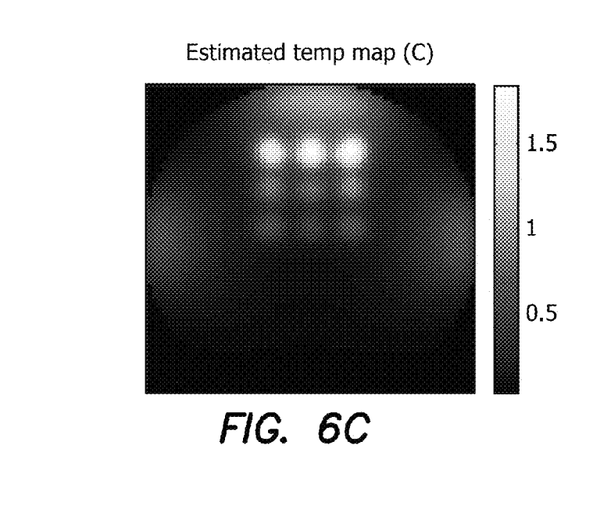
Figure 6D:
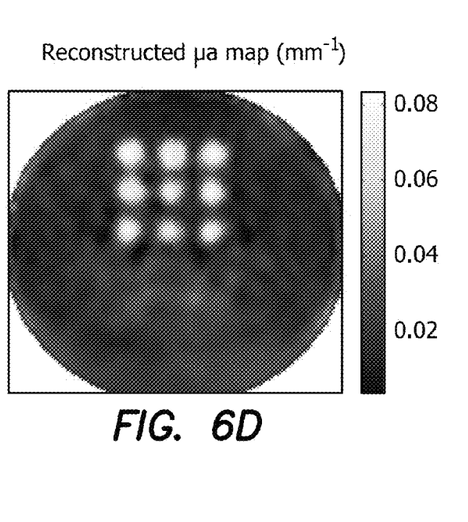

Phantom studies mimicking small animals may be undertaken. An agar based gelatin phantom is used for this purpose. The absorption and reduced scattering coefficients of the phantom are 0.01 mm$^{-1}$ and 1 mm$^{-1}$, respectively. A solid state laser emitting at 808 nm is used for illumination. Its output is coupled to three 20 m long multimode fibers of 1 mm in diameter, using a custom made fiber optic connector. The other end of the fibers is polished and fixed into a 3" long plastic probe. The laser diode controller and the laser itself is kept in an MRI control room, and the optical fiber is passed through waveguides into the MR scanner room. An animal MR/Optical imaging interface for conventional optical tomography studies is employed. The agar phantom is placed in an RF coil that is fixed in the center of the fiber interface, and the fiber probes inserted through the top and two side holes (perpendicular to the top one) on the fiber optic interface. The light output at the end of the probe may be measured with a power meter. In one embodiment, the power on the side probes was nearly one third of the top one, and the probe was held away from the phantom to obtain a spot diameter of approximately 1.5 cm. FIGS. 6a-6d show the true absorption coefficient distribution, MR temperature map and the reconstruction results respectively obtained from this embodiment, where a homogeneous phantom was used fit the coefficients used in heat equation. The true absorption map of the phantom in FIG. 6a shows the inclusions which are each 2 mm in diameter ($\mu a=0.08$ mm$^{-1}$). The temperature map obtained by forward modeling matches well with the temperature map measured with MRI. As expected the inclusions are easily resolved in MR temperature maps but they each have different temperature increases due to the spatially varying photon density. The mean absorption coefficients for each inclusion is recovered very accurately (ranging from 0.07 to 0.08 mm$^{-1}$) from the reconstructed PMI absorption map. This example demonstrates the quantitative accuracy of me proposed PIMT technique.

Example 2

Rat Imaging

Figure 1:
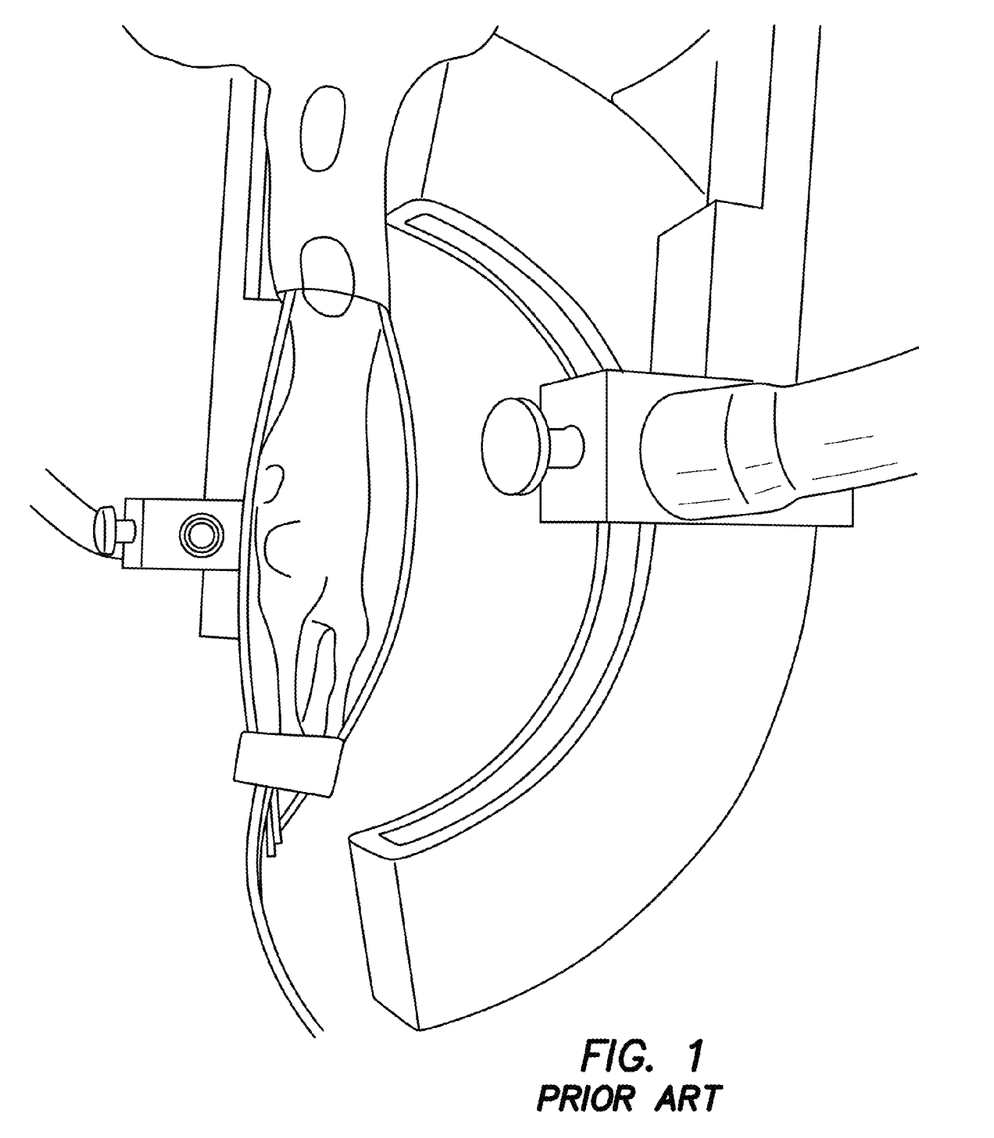
FIG. 1 shows an experimental prior art PAT setup showing the placement of a mouse in an animal holder used in one of the embodiments of the invention and illumination by a wideband ultrasonic transducer probe not used in the illustrated embodiments of the invention.
Figure 7A:
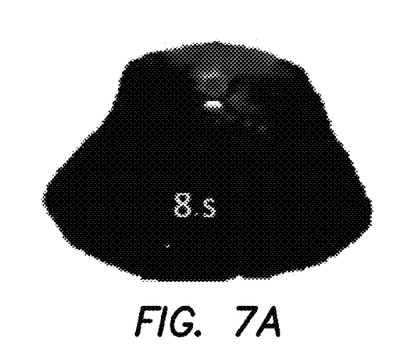
Figure 7B:
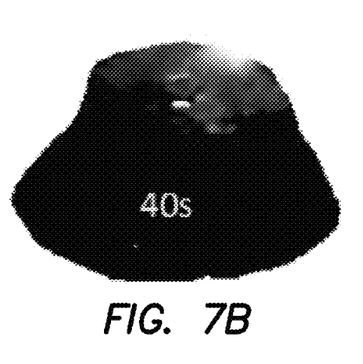
Figure 7C:
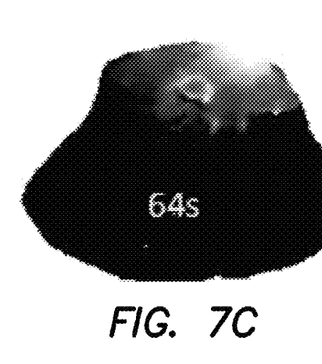
Figure 7D:
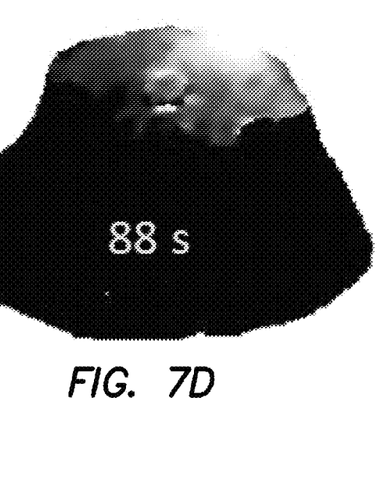
Figure 7E:
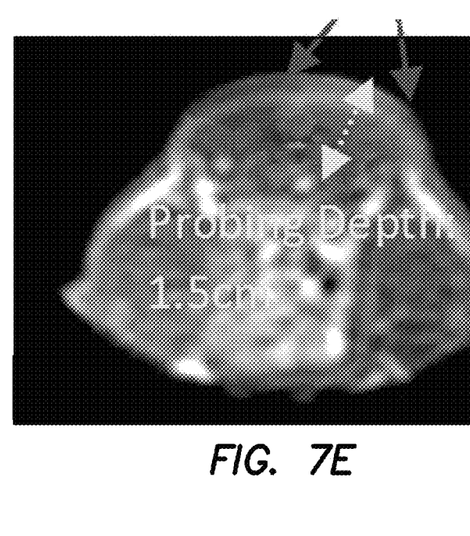

The utility of PMI in vivo is demonstrated by rat imaging with an RF coil using the experimental prior art photoacoustic tomography setup in FIG. 1. Data is acquired using a single illumination probe on top. Temperature images is acquired from a rat. As seen from FIGS. 7a-7e, data acquired from this embodiment shows that we can successfully heat the animal tissue up to 1.5 cm depth within ANSI limit. What is shown are in vivo results using a rat. These four temperature maps were obtained while the laser is on and under ANSI limit. The images of FIGS. 7d and 7e show the superimposition of anatomic image and temperature map obtained at 88s. The yellow arrow shows the probing depth, which is 1.5 cm. The red arrows indicates the illumination area. Hence, PMI is achieved for whole-body imaging of rats using illumination from multiple views. It is expected to probe much deeper in other tissues such as breast due to its lower optical absorption compared to animal tissue.

Example 3

Multiple Fiber Illumination

Figure 2:
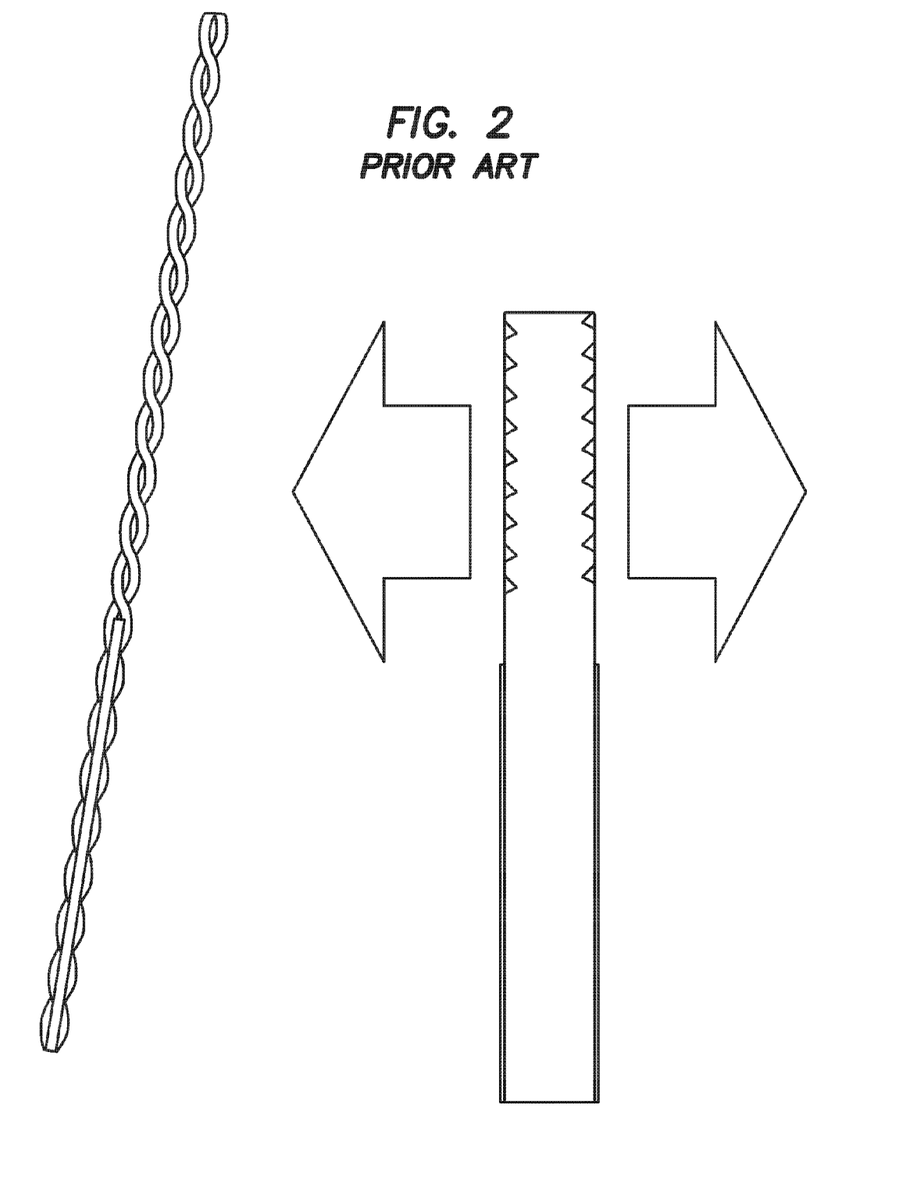
FIG. 2 is a diagram which illustrates a conventional threaded diffuser tip which is suitable for catheter based PMI.

In a further embodiment, multiple side-shooting threaded diffuser fibers are distributed inside the RF-coil around the sampling volume. FIG. 2 is a diagram of a conventional threaded diffuser tip available from Polymicro Technologies, Phoenix, Ariz., which is suitable for a catheter-based PMI approach simultaneously illuminating all surrounding tissue. This embodiment is used to implement illumination patterns within smaller volume scanners. The diffuser fibers are customized to illuminate only a half cylindrical area instead of a full cylindrical area.

Example 4

SENSE Method

In one embodiment of the present invention, a single laser diode (808 nm) and a birdcage RF-coil is used. The temporal resolution a phantom study is 10 seconds. Reducing the temporal resolution provides important benefits, in that the shorter the data acquisition time, the more diffusion-free the resulting temperature map will be. Because reconstruction takes heat diffusion into account, the resolution deteriorates as time passes. For a heating duration, MR captures the highest phase change that occurs at the end of the illumination duration and object-to-background contrast is higher in the temperature maps. Therefore, it may be seen that the sensitivity encoding (SENSE) method is adapted to photomagnetic imaging. This technique reduces total data acquisition time by under sampling the MRI data in the phase encode direction. Using this technique the full-field image is then reconstructed from the resultant aliased MR image using individual coil sensitivities. This technique has been successfully applied previously for MR-electrical impedance tomography. In this embodiment three-times SENSE acceleration may be obtained without any discernible artifacts in the phase maps compared to nonaccelerated data. It may further be shown that the SENSE method increases the temporal resolution. It is believed that better than 2 s temporal resolution may be obtained without any significant degradation in the quality of the phase maps with hardware and software (such as EPI sequence) optimization that will ultimately determine the quality of temperature maps.

Example 5

Multiple Wavelengths

The capabilities of the PMI system is demonstrated by the use of multiple wavelengths in phantom experiments where the concentrations of dyes of known spectra are determined. Example wavelengths which may be used include 680, 750, 785, 800, 808, 830, and 850 nm. In one embodiment, two suitable dyes are chosen and their spectrums are measured using an optical spectrometer. The two dyes are mixed into one or more inclusions of a phantom. The phantom may be cylindrical in shape with a diameter of 2.5 cm. These phantoms contain cylindrical inclusions of varying diameters from 1-5 mm located at different depths. The inclusions are made from agar so that there is no discontinuity in the phantom in terms of light and heat diffusion. These inclusions are made using with various concentrations of various near-infrared (NIR) optical dyes ranging from 0.5-500 µM. For a given size, different concentrations covering the above range are used to determine minimum concentration for that particular inclusion size. These measurements are repeated at different locations. After completing these measurements using a homogeneous phantom, background heterogeneities are introduced and the above measurements repeated to simulate more realistic conditions. For this purpose, multiple sections with different optical properties are embedded in the background. The data is acquired as previously described in the form of a set of MR images. After baseline images are taken, the first laser is turned on for a certain amount of time and then it is turned off, allowing MR images to be acquired during both heating and cooling-off periods. The same procedure is repeated for each laser. The whole dynamic sequence is acquired in less than 2 minutes for a single wavelength. The phase maps are then be converted into temperature maps and the optical absorption maps are reconstructed using the inverse solver. The dye concentrations in the inclusions are theme quantified from these multi-wavelength photomagnetic measurements. These concentrations are compared to the actual concentration placed into the inclusion as a function of inclusion size and location to determine the effectiveness of the system.

Example 6

Tissue Inclusions

The capabilities of the PMI system are further demonstrated by in-vivo studies which provide a more realistic background tissue distribution and background absorbance. A translucent plastic tube is used as an inclusion. The tube is filled with various concentrations of NIR dyes. Example tube diameters which may be used include 1.5, 2.0, and 3.0 mm. The length of the tube varies as well. A given size inclusion tube is filled with various concentrations of dyes at different times to cover different concentration ranges. Examples concentrations may include range from 0.5-500 µM, similar to the above embedment of phantom experiments. The inclusion is surgically implanted into an animal subject. Imaging studies are conducted immediately after surgery while the animals is still under anesthesia. The measured concentration of the optical dyes by photomagnetic imaging is compared with the actual amount implanted to determine the limits of quantification accuracy.

Example 7

Breast Sized Phantom Study

Figure 8A:
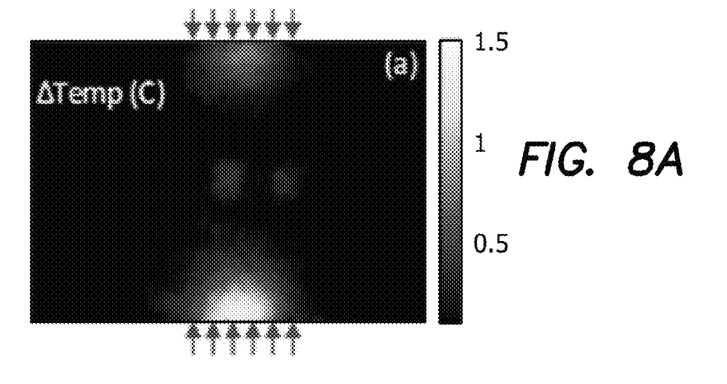
Figure 8B:
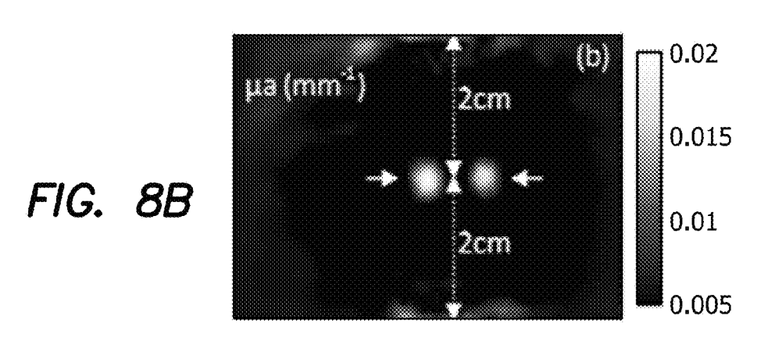
Figure 8C:
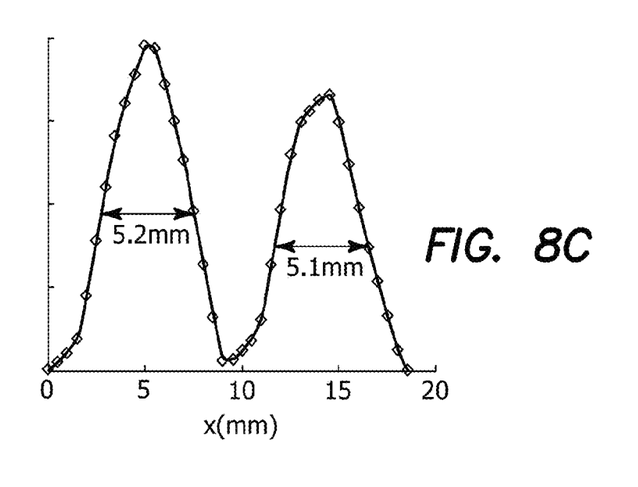

Our simulation shows that the diffusion does not degrade the resolution if the heat is continuously pumped to the tissue (i.e. when the laser is on). Based on this result, we decided to keep the laser on for a longer duration and hence, were able to keep the power under American National Standards Institute (ANSI) limit for maximum skin exposure. For this study, a similar phantom was prepared, but this time it was a rectangular one (4 cm×4 cm×6 cm) with two 5 mm inclusions positioned at the middle of the phantom to represent the worst case. The absorption and reduced scattering coefficients of the phantom were set to 0.005 mm$^{-1}$ and 1 mm$^{-1}$, respectively to imitate breast tissue. The object-to-background contrast was 4 in absorption. The phantom was illuminated from both sides within ANSI limit (3 cm diameter spot size & 2.2 W) for a duration of 32 seconds and four frames of temperature map were acquired with 8-second temporal resolution during the heating cycle. During the reconstruction, images from all four time points were used, i.e. reconstruction algorithm used the time-evolution of the temperature distribution. As seen from the FIGS. 8a-8c, both 5 mm inclusions were successfully recovered although they are located at the center of the phantom, 2 cm deep from both surfaces, which represents the worst scenario. This result confirms the potential of PMI breast imaging.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method for photomagnetic imaging of tissue comprising:
   heating the tissue using light;
   measuring a change in temperature of the tissue with magnetic resonance thermometry;
   creating an optical property map of at least one optical coefficient from the measured change in temperature; and
   determining an estimated tissue concentration of at least one of oxyhemoglobin, deoxyhemoglobin, fat, and water from the at least one optical coefficient.

2. The method of claim 1 further comprising injecting one or more temperature sensitive optical contrast agents into the tissue.

3. The method of claim 2 wherein creating an optical property map from the measured change in temperature comprises creating an optical property map based on a measure of the distribution of the injected temperature sensitive optical contrast agent.

4. The method of claim 2 further comprising evaluating the effectiveness of one or more of the temperature sensitive optical contrast agents.

5. The method of claim 1 wherein heating the tissue using light comprises heating the tissue with laser light incident upon the tissue.

6. The method of claim 1 wherein heating the tissue using light comprises heating the tissue using a continuous wave laser incident upon the tissue.

7. The method of claim 1 wherein heating the tissue using light comprises heating the tissue using laser light incident upon tissue by delivery through a flexible illuminating optical fiber.

8. The method of claim 1 wherein heating the tissue using light comprises heating the tissue using laser light delivered by a flexible illuminating optical fiber adapted to be inserted into a body cavity.

9. The method of claim 1 further comprising recovering absorption and scattering coefficients using a finite element-based inverse problem.

10. The method of claim 1 wherein creating an optical property map from the measured change in temperature comprises creating an absorption map or scattering map from the measured change in temperature.

11. The method of claim 1 further comprising using the estimated tissue concentration to diagnose a disease or to evaluate a therapeutic treatment response.

12. The method of claim 11 wherein using the estimated tissue concentration to diagnose a disease comprises using the estimated tissue concentration to diagnose a cancer which is determined as benign or malignant based on the determined data.

13. The method of claim 1 further comprising determining a metabolic property of tissue from the determined estimated tissue concentration.

14. An apparatus for performing photomagnetic imaging of tissue comprising:
   a light source to heat the tissue;
   a magnetic resonance imaging system to measure a change in temperature of the tissue; and
   a data processor to generate an optical property map of at least one optical coefficient from the measured change in temperature and to determine an estimated tissue concentration of at least one of oxyhemoglobin, deoxyhemoglobin, fat, and water from the at least one optical coefficient.

15. The apparatus of claim 14 where the data processor is configured to diagnose a disease or to evaluate a therapeutic treatment response based on the estimated tissue concentration.

16. The apparatus of claim 15 wherein the data processor uses the estimated concentration to diagnose a cancer which is determined as benign or malignant based on the determined data.

* * * * *

UNITED STATES PATENT AND TRADEMARK OFFICE
CERTIFICATE OF CORRECTION

PATENT NO. : 9,078,587 B2  
APPLICATION NO. : 13/654346  
DATED : July 14, 2015  
INVENTOR(S) : Gultekin Gulsen Page 1 of 1

It is certified that error appears in the above-identified patent and that said Letters Patent is hereby corrected as shown below:

Specification

In column 1 at line 6, Change "2012," to --2011,--.

In column 1 at line 35, Change "Furthermore." to --Furthermore,--.

In column 4 at line 56, Change "processer" to --processor--.

In column 11 at line 23 (approx.), Change "theme" to --then--.

Claims

In column 14 at line 38 (approx.), In Claim 16, change "processer" to --processor--.

Signed and Sealed this
Sixteenth Day of August, 2016

Michelle K. Lee
*Director of the United States Patent and Trademark Office*